United States Patent [19]
Alonso

[11] Patent Number: 5,037,377
[45] Date of Patent: Aug. 6, 1991

[54] MEANS FOR IMPROVING BIOCOMPATIBILITY OF IMPLANTS, PARTICULARLY OF VASCULAR GRAFTS

[75] Inventor: Manuel T. Alonso, Newport Beach, Calif.

[73] Assignee: Medtronic, Inc., Minneapolis, Minn.

[21] Appl. No.: 898,686

[22] Filed: Aug. 21, 1986

Related U.S. Application Data

[60] Division of Ser. No. 675,721, Nov. 28, 1984, which is a continuation-in-part of Ser. No. 520,986, Aug. 8, 1983, abandoned, which is a continuation-in-part of Ser. No. 303,345, Oct. 7, 1981, abandoned.

[51] Int. Cl.$^5$ .............................................. A61F 2/06
[52] U.S. Cl. ................................. 600/36; 128/DIG. 8
[58] Field of Search ............... 623/1, 66; 128/DIG. 8; 600/36

[56] References Cited

U.S. PATENT DOCUMENTS

| | | | |
|---|---|---|---|
| 3,425,418 | 2/1969 | Chuapil et al. | 623/1 |
| 4,164,524 | 8/1979 | Ward et al. | 623/1 X |
| 4,167,045 | 9/1979 | Sawyer | 623/1 |

FOREIGN PATENT DOCUMENTS

| | | | |
|---|---|---|---|
| 2601289 | 7/1977 | Fed. Rep. of Germany | 623/1 |
| 0190966 | 9/1985 | Japan | 623/1 |
| 0904693 | 2/1982 | U.S.S.R. | 623/1 |

Primary Examiner—Alan Cannon
Attorney, Agent, or Firm—Reed A. Duthler

[57] ABSTRACT

Implants containing a reasonably biocompatible fabric, which is to be exposed to blood flow after implantation, are rendered biocompatible and substantially impervious to blood, by applying a collagen composition containing soluble collagen, and preferably also collagen fibers, to the fabric in such a manner that the collagen composition penetrates into the interstitial spaces of the fabric. The fabric retaining collagen composition is then incubated at elevated temperature for sufficient time to form collagen fibers from the soluble collagen. Thereafter, the implant is dried. The steps of applying collagen composition, incubating and drying are repeated approximately two to four times. The implants, particularly when they comprise tubular vascular grafts, are tested for porosity by placing a pressurized column of aqueous solution, such as saline, into their interior. When the implant is sufficiently impervious to liquid, it is treated with a suitable cross-linking agent, such as glutaraldehyde solution, to bond adjacent collagen fibers to one another. When the implants are tubular vascular grafts, the treatment with glutaraldehyde is conducted in a longitudinally extended position of the graft, and with a pressurized column of glutaraldehyde placed within the interior of the tubular grafts.

15 Claims, 2 Drawing Sheets

MEANS FOR IMPROVING BIOCOMPATIBILITY OF IMPLANTS, PARTICULARLY OF VASCULAR GRAFTS

This is a divisional of co-pending application Ser. No. 675,721 now filed on Nov. 28, 1984, now abandoned, which is a C-I-P of Ser. No. 520,986 filed Aug. 8, 1983, now abandoned, which is C-I-P of Ser. No. 303,345 filed Oct. 7, 1981, now abandoned.

TECHNICAL FIELD

The present invention relates to improving biocompatible materials for cardiovascular and arterial grafts and, more specifically, to fabric materials made impervious and yet more compatible with biological tissues. These fabrics are used routinely in conjunction with heart valve prostheses, cardiovascular patches, blood filters, vascular grafts, oxygenators and reservoirs, and more recently they are made integral with plastic structural materials for prostheses such as valve stents and sewing rings. In accordance with the present invention, the attachment of collagen fibers grown in the interstices of the fabric, provide the desired flexibility, imperviousness, and biocompatibility.

BACKGROUND OF THE INVENTION

The prior art does not show the use of collagenated fabric wherein collagen fibers are chemically attached to fabric materials. Although it is well known that collagen developed from bovine tissue is not rejected from the human body and indeed, is used in plastic surgery extensively for filling in local bone or tissue defects by injection of collagen, making a more natural skin appearance, and is often used in removing facial lines, particularly "crow's feet" around the eyes, the use of these fibers had not been proposed for making area coverings, such as vascular grafts or heart valve prostheses. The state of the art prior to the invention is generally described in two publications by A. L. Rubin, et al.: "The Structure and Use of Collagen" in Biomaterials, pp. 157-184 (1969) and "Collagen Materials In Dialysis and Implantation", Transactions of the American Society of Artificial Organs, 14; 169-174 (1968).

In addition, a collagen impregnated vascular graft is described in U.S. Pat. No. 4,319,363. The vascular graft or implant of this prior art patent is obtained by implanting a rod or tube in a live host animal, such as sheep. Thereafter, collageneous tissue is allowed to grow on the implant to form a coherent tubular wall. The rod, covered by tissue, is then removed from the host animal, the collagenous tissue is removed from the rod and is tanned in glutaraldehyde to serve as the vascular graft.

DISCLOSURE OF THE INVENTION

The present invention teaches the use of collagen in combination with superfine mesh fabrics; knitted, braided or woven. Thus, collagenated material can drastically reduce the stenosis of a prosthesis by substantially reducing the cross-sectional profile, reducing thick layers of fibrous tissue which would normally overgrow the fabric not treated with collagen.

In the case of a vascular graft, a collagenated fabric, i.e., a graft mesh of approximately 40 microns porosity or more, is used, into which collagen fibers reconstituted from purified natural collagen are grown. Thereafter, the collagen fibers are chemically and/or physically bonded to each other and to the polyester fabric material, by bathing the collagenated fabric in a buffered solution of glutaraldehyde or formaldehyde.

Experiments have been performed on laboratory animals and lifecycle tests have been made using mechanical instrumentation, indicating that, in a vascular graft, the flexibility is not impaired by the interstitial collagen and there is characteristically no buildup of stenotic layers.

In contrast to the above-summarized invention in the prior art polyester (DACRON), vascular grafts generally require some form of preclotting with non-heparinized whole blood to minimize the risk of uncontrolled bleeding after implantation. The preclotting procedure is commonly performed by immersion of the graft in non-heparinized whole blood from the patient. Although this technique is widely accepted, it is not free of secondary complications. In addition to variability in blood retention capacity, the immersion method leaves the graft lumen highly thrombogenic due to the presence of high concentrations of thrombin. A second method of preclotting, using platelet-rich plasma and heating the saturated graft, has also been developed in the prior art. This method appears to achieve more reliable sealing initially but lysis of the interstitial clots by heparinized blood may occur resulting in massive and possibly fatal bleeding. While conventional DACRON grafts have frequently been used in the successful replacement of large arteries over a long period of time, poor or variable healing of the graft luminal wall surface may be commonly observed and the graft is at some risk of thrombotic occlusion due to a chronic tendency to form a fabric-thrombus complex.

Therefore, the present invention provides a method for eliminating the preclotting step in vascular grafts without altering their handling properties. It also improves the blood compatibility of the graft lumen surface.

Accordingly, it is an object of the invention to provide a greatly improved prosthesis material for interfacing with living tissue, by the addition of collagen fibers to the commonly used polyester or like biocompatible fabric.

Another object of the invention is to provide a vascular prosthetic material that facilitates operative procedures, requiring no time or little time in saturating the fabric with blood constituents before implantation.

Still another object of the invention is to provide a prosthetic fabric which substantially reduces the likelihood of buildup of thrombotic material.

The foregoing and other objectives, characteristics, and features of the invention will be better understood by reading the following detailed description in conjunction with the appended drawings.

DETAILED DESCRIPTION OF THE INVENTION

Figure 1:
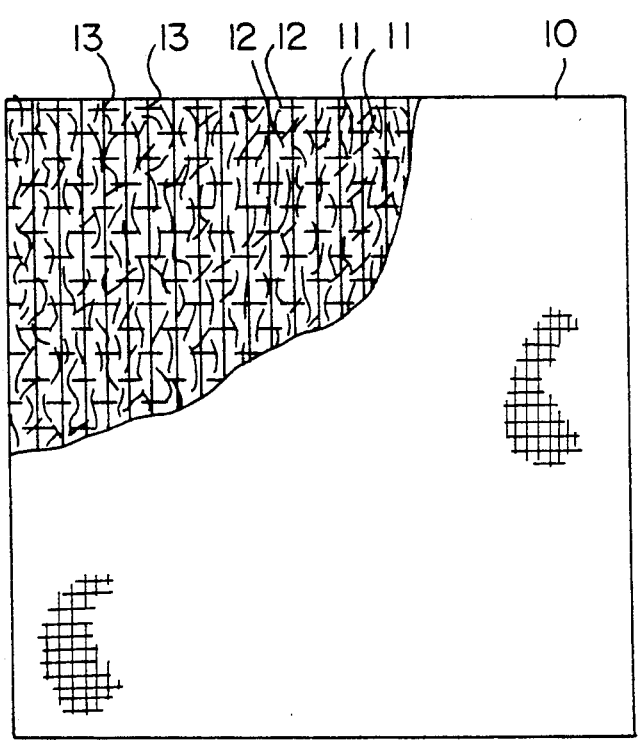
FIG. 1 is a drawing of an artificial vascular and patch graft material comprising a flexible elastic fabric substrate. Of predetermined shape and having fibrous collagen adhering to the walls and interstices of the fabric.
Figure 2:
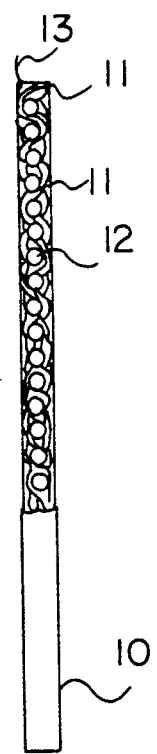
FIG. 2 is a cross-sectional view of the collagenated fabric.

Referring to FIG. 1, a section of a vascular graft shows the intertwining of the small diameter collagen strands 11 with the preformed cloth 10. In the present embodiment, a microporous woven fabric, consisting of woven strands 12 and 13 of polyester or other biocompatible materials, forms the substrate. However, any type of biocompatible mesh, including braided or knitted, may be used. The intertwining is the result of natural growth processes of the collagen fibers when incubated. In one preferred embodiment of the present invention, the fabric 10 comprises the structural material of a tubular, usually corrugated, vascular graft 12, schematically shown on FIG. 3. Such vascular grafts are usually of approximately 4 to 30 millimeter internal diameter.

It should be noted that in another preferred embodiment of the present invention the fabric 10 can be formed integrally with structural members of a prosthesis, such as valve prosthesis (not shown) in which the fabric is attached at the time of the molding of a stent (not shown) and sewing ring (not shown).

The collagen is adhered to the polyester or other biocompatible fabric in accordance with the following procedure.

Bovine skin (not shown) is cleaned, trimmed, and flesh is removed from the skin. The skin is cut into strips and immersed in acetic acid. The saturated skin is homogenized in a homogenizer and then diluted in 0.05 mol acetic acid and then centrifuged at low temperature. The resulting slurry is then salt (NaCl) precipitated and re-centrifuged to obtain a collagen paste. The paste is then diluted in buffer solution to adjust the pH factor to 7.4. The product obtained in this manner is called acidity adjusted soluble collagen, or simply soluble collagen.

Collagen fibers are obtained from soluble collagen by incubating (maintaining) soluble collagen at 37 degrees centigrade until the solution becomes a gel.

In accordance with one method of the invention, the fabric of the prosthesis is impregnated with soluble collagen. However, in accordance with the preferred embodiment of the invention, the fabric of the prosthesis is impregnated with a mixture of soluble collagen and collagen fibers (hereinafter collagen mixture).

The collagen mixture is prepared by mixing, preferably equal volumes of soluble collagen and collagen fibers. Thereafter, the mixture is homogenized to obtain collagen particles, preferably in the range of approximately 25 to 250 microns.

The impregnation of the fabric is conducted by applying soluble collagen, or preferably collagen mixture, to the fabric, and by thereafter incubating the collagen coated fabric at 37 degrees centigrade. The incubation reconstitutes the collagen fibers on the fabric.

Preferred methods of applying soluble collagen, or most preferably, collagen mixture, to vascular grafts are vacuum impregnation and impregnation under pressure.

In the vacuum impregnation process the tubular vascular grafts 12 (which are highly porous in their unimpregnated form) are plugged at one end and are filled with soluble collagen, or preferably with the collagen mixture. The grafts are kept in a vessel (not shown) which is evacuated to obtain a pressure differential in the physiological pressure range, preferably approximately 120 millimeters of mercury (Hgmm). The pressure differential forces the collagen to flow through the pores of the fabric 10. Thereafter, the graft is incubated at 37 degrees centigrade, as noted above. Typically, the step of incubation is conducted in such a manner that the actual temperature of the grafts is maintained at 37 degrees centigrade for approximately twenty minutes. Thereafter, the grafts are dried for approximately twenty minutes.

The steps of vacuum impregnation, incubation, and drying are repeated until tests with saline under physiological pressure (typically 120 Hgmm) show the grafts to be sufficiently impervious to liquid. Usually, the steps of vacuum impregnation, incubation, and drying must be repeated approximately two to four times (most typically three times) to obtain substantially liquid impervious grafts.

In the process of impregnation under pressure, which is preferred over vacuum impregnation, the tubular grafts are plugged at one end. Thereafter, soluble collagen, or preferably collagen mixture, is placed under physiological pressure (usually 120 Hgmm) into the tubular grafts. The pressure causes the collagen to flow through the fabric of the graft. After pressurization, the vascular grafts are incubated and dried as described in connection with the vacuum impregnation process. The process of impregnation under pressure, incubation, and drying is repeated until tests show that the graft is substantially impervious to liquid under physiological pressure. Usually, the procedure must be repeated two to four, most often three, times.

When the grafts are sufficiently impervious to liquid, they are immersed in a solution of glutaraldehyde for cross-linking and deprivation of the antigenicity properties of the foreign animal proteins.

More particularly, treatment with 0.35 percent (by weight) or like concentration aqueous glutaraldehyde solution of approximately 7.4 pH is used to cross-link the collagen fibers with one another.

Preferably, the corrugated vascular grafts are treated with glutaraldehyde solution in a longitudinally extended position. Still more preferably, the treatment with glutaraldehyde includes placing the glutaraldehyde solution inside the graft under physiological pressure. These features of the process of the present invention are particularly advantageous because they result in vascular grafts which have very good properties of imperviousness. If the vascular grafts were not treated with glutaraldehyde in longitudinally extended position, or under pressure, then, in some instances, the collagen might separate from the fabric during the surgery of implantation or under the patient's natural blood pressure, resulting in disastrous graft failure.

As is known, treatment with glutaraldehyde links the collagen fibers to one another, because it causes covalent chemical bond bridges to form between several protein chains of the fibers. The vascular grafts of the invention are usually stored and transported in glutaraldehyde or saline solution.

Figure 3:
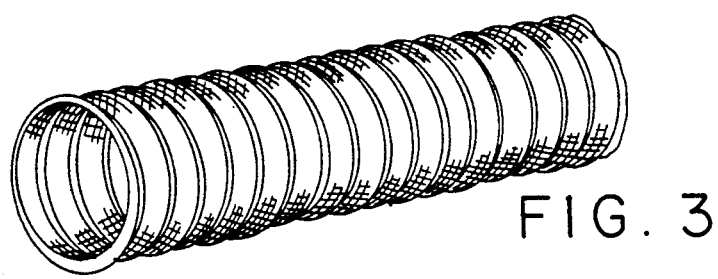
FIG. 3 is a schematic perspective view of a vascular graft made in accordance with the present invention.

The graph of FIG. 3 shows the result of a fibrinogen sorption test conducted with human blood and with a sample of the material of the collagenated vascular graft of the present invention, and with a sample of "prior art" uncollagenated polyester vascular graft material. As is known by those skilled in the art, the greater the fibrinogen sorption of the graft material, the greater is its thrombogenicity. The self-evident data of the graph reveal that the collagenated vascular graft of the present invention is significantly less thrombogenic than the "prior art" untreated vascular graft material.

Figure 4:
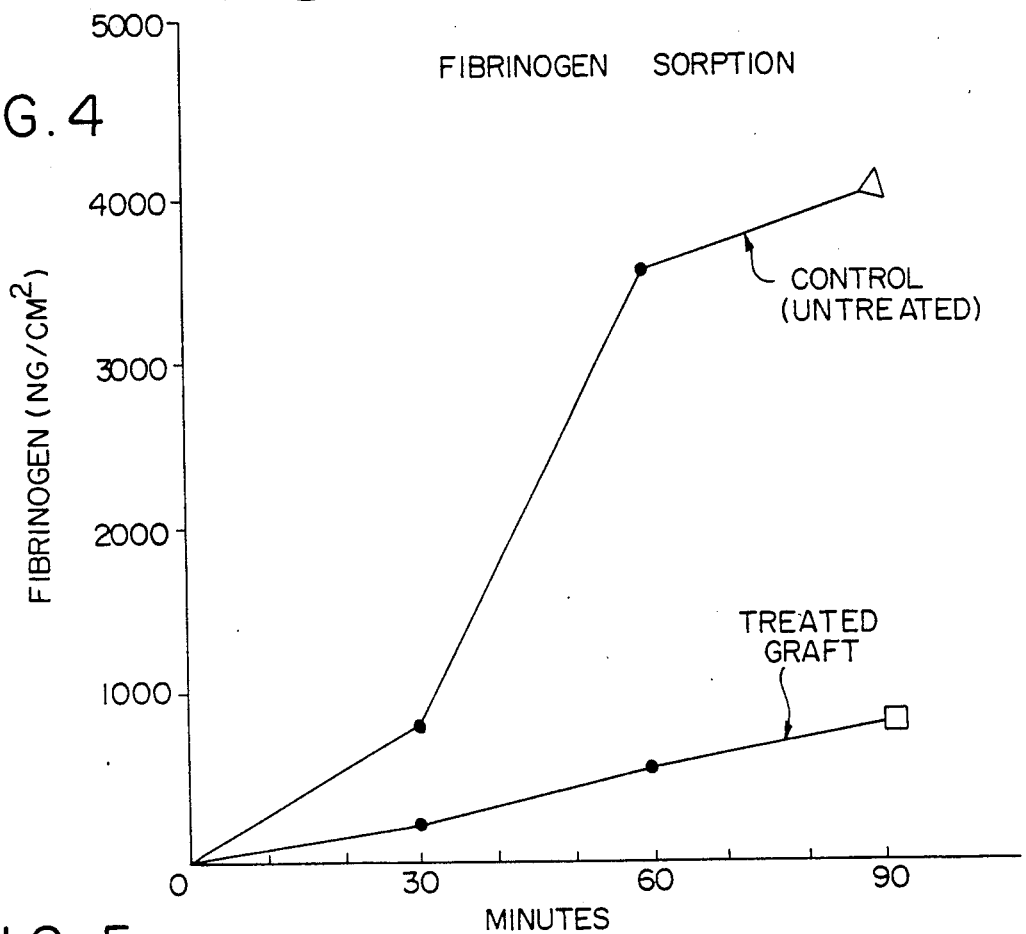
FIG. 4 is a graph showing fibrinogen sorption tests conducted with vascular graft material of the present invention and with a prior art vascular graft material.
Figure 5:
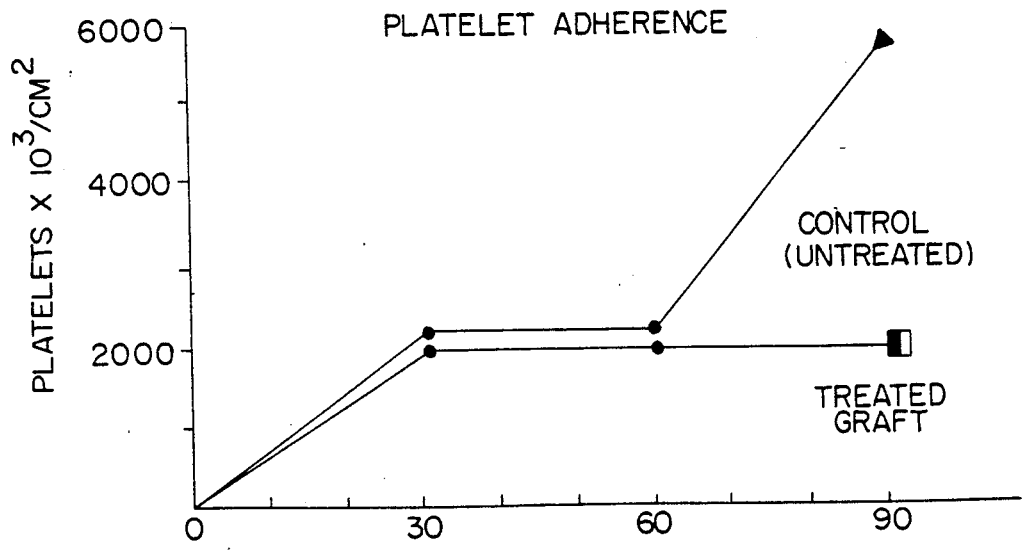
FIG. 5 is a graph showing platelet adherence tests conducted with vascular graft material of the present invention and with prior art vascular graft material.

Similar results, indicating significantly less thrombogenicity of the vascular graft material of the present invention than of prior art untreated grafts, are revealed by platelet adherence tests, as shown in FIG. 4.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A process for making a prosthetic material adapted for implantation into the human body in contact with blood flow in the human vascular system, the process comprising the steps of:

applying a solution of collagen to a reasonably biocompatible fabric which has interstitial spaces;

incubating the fabric having the applied collagen solution at an elevated temperature to obtain collagen fibers as a coating and in the interstitial spaces of the fabric, and treating the fabric having collagen fibers with a solution of an aldehyde cross-linking agent to bond the fibers to one another.

2. The process of claim 1 wherein the steps of applying collagen and incubating are repeated several times.

3. The process of claim 1 further comprising the step of substantially drying the collagen fiber containing fabric after the step of applying.

4. The process of claim 1 wherein, in the step of treating the aldehyde, the cross-linking agent is glutaraldehyde.

5. A process for making a vascular graft having a tubular fabric base which has interstitial spaces wherethrough liquid can flow from the interior of the tubular base to its exterior, the process comprising the steps of:

applying a collagen composition containing soluble collagen to the fabric base and forcing the collagen solution to enter into the interstitial spaces of the fabric;

incubating the fabric base having the applied collagen composition at an elevated temperature for sufficient time to form collagen fibers from the predominant majority of the collagen solution retained in the fabric, and thereafter treating the fabric base having the collagen fibers with a solution of an aldehyde cross-linking agent to form chemical bonds between adjacent fibers of collagen.

6. The process of claim 5 wherein the steps of applying collagen and incubating are conducted approximately two to four times.

7. The process of claim 5 wherein each step of applying and forcing collagen composition and subsequent step of incubating is followed by a step of drying the collagenated fabric base.

8. The process of claim 6 wherein in the step of applying and forcing, the collagen composition is forced into the interstitial spaces of the fabric by a differential existing between the pressure of the collagen composition present in the interior of the tubular vascular graft and the pressure which exists on the outside of the tubular graft.

9. The process of claim 8 wherein the collagen composition is pressurized in the interior of the tubular graft above ambient pressure.

10. The process of claim 8 wherein the collagen composition is maintained at approximately ambient pressure within the interior of the tubular graft, and wherein the pressure prevailing on the exterior of the tubular graft is decreased below ambient pressure.

11. The process of claim 8 additionally comprising at least one step of testing the porosity of the vascular graft having the collagen in the interstitial spaces of the fabric base by placing a pressurized column of aqueous solution into the interior of the tubular graft.

12. The process of claim 6 wherein the collagen composition comprises a mixture of soluble collagen and collagen fibers.

13. The process of claim 12 wherein the collagen composition comprises approximately equal volumes of collagen fibers and soluble collagen.

14. The process of claim 6 wherein during the step of treating, the tubular vascular graft is maintained in a substantially longitudinally extended position.

15. The process of claim 14 wherein the solution of the cross-linking agent is forced by pressure from the interior of the tubular base into the interstitial spaces of the fabric.

* * * * *